(12) United States Patent
Ewaschuk

(10) Patent No.: US 7,862,553 B2
(45) Date of Patent: Jan. 4, 2011

(54) TIP AND SHAFT CONNECTION FOR MEDICAL DEVICE

(75) Inventor: Michael Ewaschuk, Haverhill, MA (US)

(73) Assignee: Microline Surgical, Inc., Beverly, MA (US)

( * ) Notice: Subject to any disclaimer, the term of this patent is extended or adjusted under 35 U.S.C. 154(b) by 1428 days.

(21) Appl. No.: 11/179,509

(22) Filed: Jul. 13, 2005

(65) Prior Publication Data

US 2007/0073247 A1 Mar. 29, 2007

(51) Int. Cl.
*A61B 17/00* (2006.01)
(52) U.S. Cl. .......................................... 606/1; 604/264
(58) Field of Classification Search ................. 604/264; 606/1
See application file for complete search history.

(56) References Cited

U.S. PATENT DOCUMENTS

| | | | | |
|---|---|---|---|---|
| 4,011,830 A * | 3/1977 | Anderson et al. | ............. | 118/60 |
| 4,927,416 A * | 5/1990 | Tomkiel | ...................... | 604/198 |
| 5,086,780 A * | 2/1992 | Schmitt | ...................... | 600/576 |
| 5,342,379 A * | 8/1994 | Volinsky | ...................... | 606/167 |
| 5,423,758 A * | 6/1995 | Shaw | ......................... | 604/110 |
| 5,593,402 A * | 1/1997 | Patrick | ......................... | 606/1 |
| 5,810,864 A * | 9/1998 | Schaller | ...................... | 606/170 |
| 5,893,875 A * | 4/1999 | O'Connor et al. | ........... | 606/205 |
| 6,464,711 B1 * | 10/2002 | Emans et al. | ................ | 606/167 |
| 6,544,277 B1 * | 4/2003 | O'Heeron et al. | ........... | 606/185 |
| 6,629,983 B1 * | 10/2003 | Ignon | ......................... | 606/131 |
| 6,916,314 B2 * | 7/2005 | Schneider et al. | ............... | 606/1 |

OTHER PUBLICATIONS

U.S. Appl. No. 11/188,704 to Ewaschuk, which was filed on Jul. 26, 2005.
U.S. Appl. No. 11/189,789 to Theroux et al., which was filed on Jul. 27, 2005.

* cited by examiner

*Primary Examiner*—Henry M Johnson, III
*Assistant Examiner*—Aaron Roane
(74) *Attorney, Agent, or Firm*—Greenblum & Bernstein, P.L.C.

(57) ABSTRACT

A medical device includes a tube end to which a tip having a medical tool is attached. The tip includes a tip housing and a lock tab, as well as a yoke. The tube end includes an outer tube and an inner shaft, in which the inner shaft engages the yoke and the outer tube engages the tip housing. The lock tab fits into a recess in the outer tube to prevent twisting of the tip when engaged with the tube end, and the yoke includes a locking ring to which a spring protrudes, to fixedly and detachably connect the tip to the tube end.

40 Claims, 5 Drawing Sheets

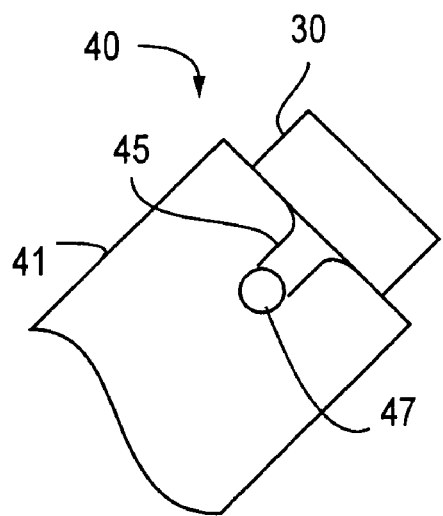
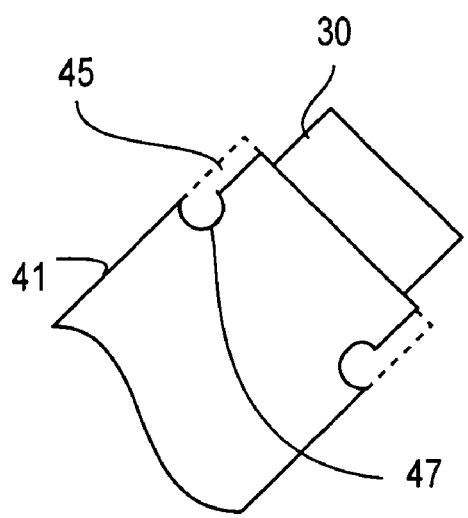
FIG. 3A                FIG. 3B
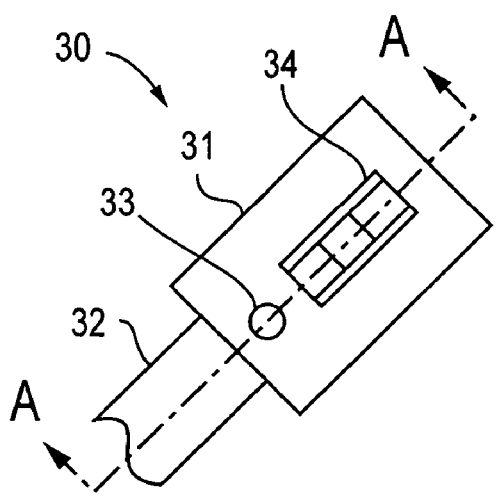
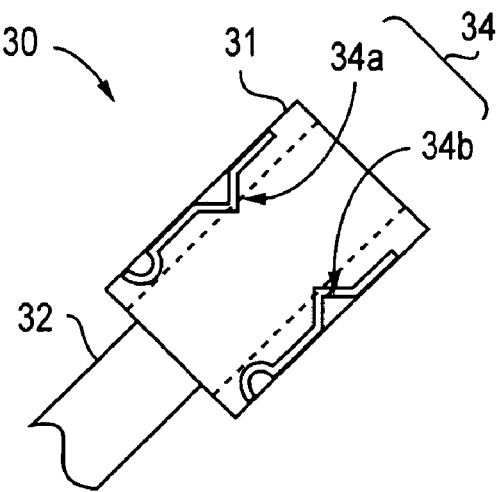
FIG. 4A                FIG. 4B

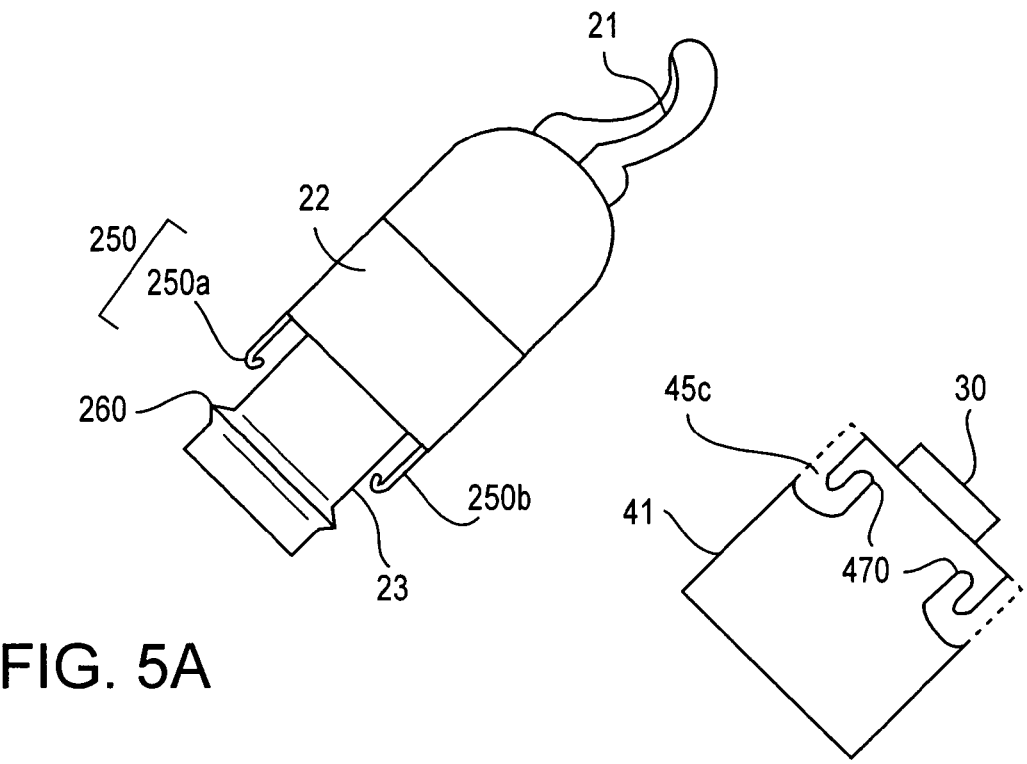
FIG. 5A
FIG. 5B
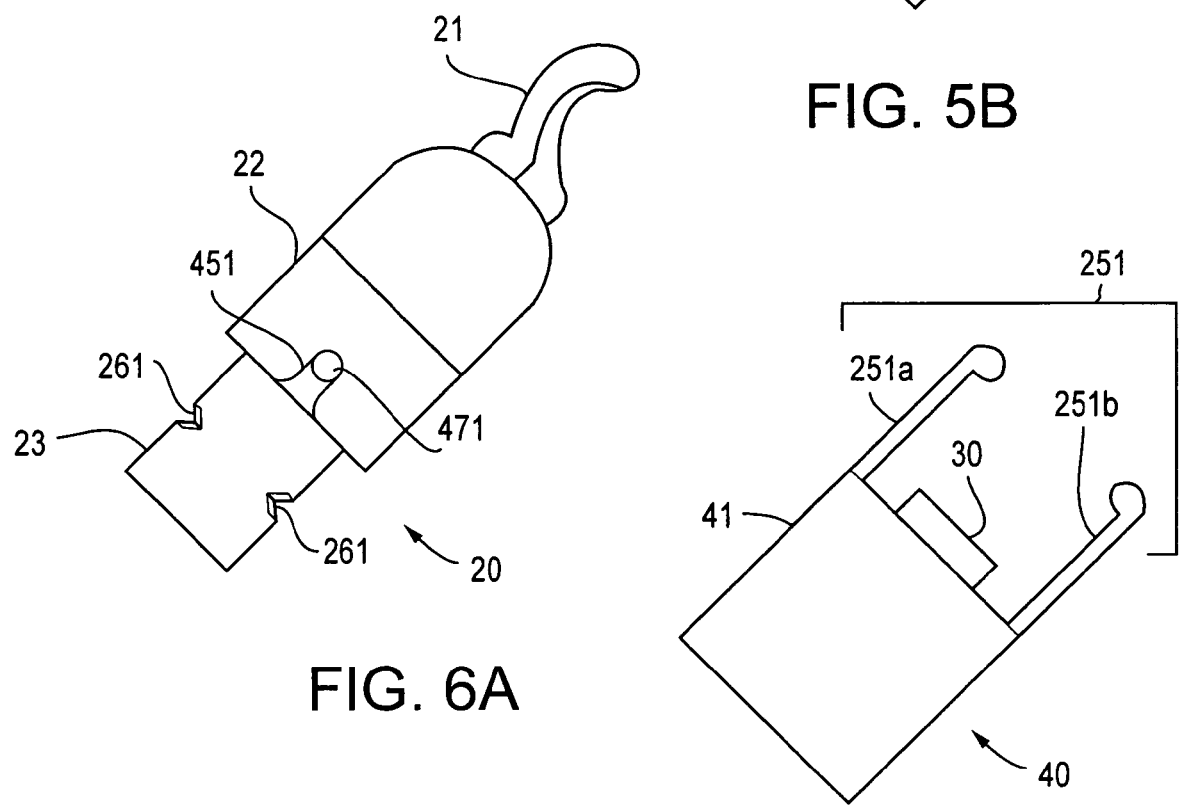
FIG. 6A
FIG. 6B

TIP AND SHAFT CONNECTION FOR MEDICAL DEVICE

BACKGROUND OF THE INVENTION

1. Field of the Invention

The present invention relates to a medical device having a detachable tip for engaging a tube end, and more particularly to a connection mechanism for attaching a tool-bearing tip to a distal tube end of a surgical or medical device.

2. Background

Medical and surgical instruments such as cauterization tools, laparoscopes, electrified instruments and the like which generally include a tube having a distal end onto which a tip is attached, the tip including a tool for the medical or surgical procedure to be performed, and a proximal end for connection to mechanical and/or electrical systems and which is operated by the surgeon or medical technician performing the procedure, have been widely used because the incision necessary for insertion of such a tool on a medical device is typically small in comparison to alternative methods. As a result of the relatively smaller incision, patients typically exhibit more rapid healing times and often experience fewer complications as a result of surgeries using such medical devices.

A typical medical device of this class may include at least two detachable portions—the tip having the tool as one of the detachable portions, and the tube leading from the distal end back to the proximal end as the other. Further, such medical devices may include an inner tube leading from the proximal end to the tube end of the tube at the distal end for connecting to a yoke which is part of the detachable tip. Because proper operation of the tool on the tip may require precise mechanical shifting of the inner tube and yoke in relation to the tube and housing of the tip, one method that has been used to provide the necessary differentiation when connecting the tip to the tube end has been the use of two sets of threading with mutually differential pitches, respectively on the connections between the yoke of the tip and the inner shaft of the tube end on the one hand, and a housing or casing of the tip and an outer tube of the tube end, on the other hand.

As a result, however, the two threadings of different pitches require fine machining during the manufacturing process, within tolerances that are difficult to achieve using automation and which may tend to increase the cost of manufacturing of such medical devices. For example, after an initial machining of the threading, it may be necessary to test and make adjustments several times by hand, which requires skilled machinists as well as additional iterative steps, which increase the time for manufacture considerably.

Furthermore, the use of threading requires the surgeon or medical technician performing a procedure with the medical device to intricately align the two threadings of different pitch when assembling the tip to the tube end. Such an operation may increase the time necessary to detach and/or reattach tips to tube ends during a medical procedure and therefore increase the costs and medical risks of the medical procedure, for example.

Also, if fluid or other material contaminates the fine threading of the tip or tube end, it may be difficult to adequately clean or sterilize the crevices in the convoluted surface of the threading. Moreover, such contamination may be shielded from autoclaving or sterilization, for example.

BRIEF SUMMARY OF THE INVENTION

In view of the above-noted issues, and other issues, the present invention relates to a medical device in which a tip is detachably connected to a tube end, without necessarily using threading. According to an aspect of the present invention, the medical device may include a tube end having an outer tube and an inner shaft, a recess disposed in the outer tube, an instrument tip engageable with the tube end and having a lock tab to engage with the recess of the tube end and a yoke to engage with the inner shaft of the tube end, a locking ring located on one of the yoke and the inner shaft, and a spring located on the other of the yoke and the inner shaft to engage the locking cavity. As an advantage, it may be possible to attach and/or detach the tip from the tube end by a push/pull operation, rather then by aligning threading, for example.

The medical device may further include another recess disposed in the outer tube of the tube end, and another lock tab disposed on the tip to engage with the other recess of the outer tube of the tube end; a cuff attached to the inner shaft and including the spring fixedly attached to an interior of the cuff, to receive the yoke, in which the spring engages the locking ring when the tip is engaged with the tube end; another spring to engage the locking ring; a rounded detent portion disposed at an extremity of the lock tab of the tip to engage with a divot disposed at an extremity of the recess of the outer tube of the tube end. Further, the locking ring may have a notched profile and generally extend around a circumference of the yoke; the recess of the outer tube of the tube end may have a shape generally similar to a letter "L"; or the recess of the outer tube of the tube end may have a generally linear outline extending from an edge of the outer tube to resist twisting of the tip relative to the tube end. Furthermore, the lock tab may be radially biased toward a longitudinal center of the tip.

According to another aspect of the present invention, the medical device may include a tube end including an outer tube end and an inner shaft, an instrument tip engageable with the tube end and including a yoke to engage the inner shaft of the tube end, a recess located on one of the tip and the outer tube end, a lock tab located on the other of the tip and the outer tube end to engage the recess, and a lock which includes: a protrusion located on one of the tube end and the yoke, and a concavity located on the other of the tube end and the yoke, in which the protrusion and the concavity may engage each other to secure the tip to the tube end.

The protrusion may be disposed in the yoke and include a spring to elastically extend toward the outer tube of the tube end; the concavity may be disposed in the tube end and include a spring to receive the protrusion, the protrusion being disposed on the yoke; the lock tab may be radially biased toward the other of the tip or the tube end; or the lock tab may be connected to the outer tube of the tube end, with the recess disposed in the tip.

According to these and other aspects of the present invention, a medical device may inhibit twisting of the tip relative to the tube end by virtue of the engagement of the lock tabs with the respective recess in either the tube end or the tip, while maintaining the tip attached to the tube end by the engagement of the locking ring or locking protrusion on the yoke of the tip with the spring or locking member of the tube end, which may be disengaged by an appropriate push and/or pull of the tip from the tube end to disengage the tip from the tube end without necessarily using threading, for example. Furthermore, because these and other aspects of the present invention may typically include fewer crevices or other convoluted surfaces which may harbor contamination, the sterilization or cleansing of the various tips and tube ends of the medical device according to these aspects may be facilitated and their effectiveness enhanced relative to other engagement technologies such as threading, for example. In addition, the tool of the tip may be any appropriate tool used in a surgical or medical procedure and suitable for use in such a medical device, and is not necessarily limited to tools for cauterization, excision or laparoscopy, although these types of tools may also be used.

Other exemplary embodiments and advantages of the present invention may be ascertained by reviewing the present disclosure and the accompanying drawings.

BRIEF DESCRIPTION OF THE DRAWINGS

The present invention is further described in the detailed description which follows, in reference to the noted drawings by way of non-limiting examples of certain embodiments of the present invention, in which the numerals represent like elements throughout the several view of the drawings, in which:

FIG. 3A is an enlarged view of a tube end of the medical device shown in FIG. 1;

FIG. 3B is a side view of the tube end shown in FIG. 3A;

FIG. 4A is an enlarged view of an inner shaft of the tube end shown in FIGS. 3A and 3B;

FIG. 4B is a cutaway view of the inner shaft shown in FIG. 4A, illustrating an interior of the inner shaft;

FIG. 5A is a perspective view illustrating a tip of a medical device according to a second embodiment of the present invention;

FIG. 5B is an enlarged view illustrating a tube end of the medical device according to the second embodiment;

FIG. 6A is a perspective view of a tip according to a third embodiment of the present invention;

FIG. 6B is an enlarged view of a tube end according to the third embodiment;

DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
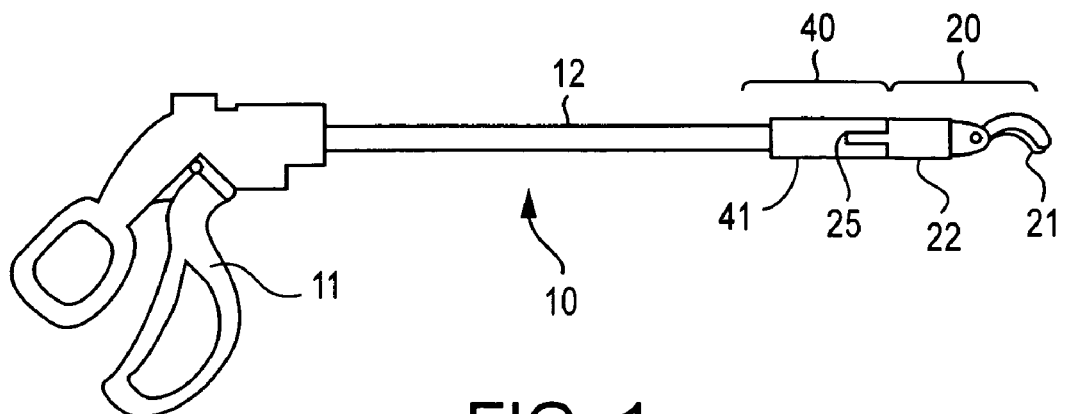
FIG. 1 is a perspective view illustrating a medical device according to a first embodiment of the present invention.

FIG. 1 illustrates a medical device 10 having a tube 12 and a handle 11 at the proximal end of the tube 12. At the distal end of the tube 12 is a tube end 40 having an outer tube 41, to which a tip 20 is attached. The tip 20 includes a tool 21 to perform a medical or surgical function on a patient, and is typically inserted into an area in which surgery is to be performed while attached to the tube end 40 of the medical device 10. Among the various tools which may be part of the tip 20 are, for example, electrified scalpels, shears, grasping tools, cauterization tools, laparoscopic tools, and the like.

Figure 2A:
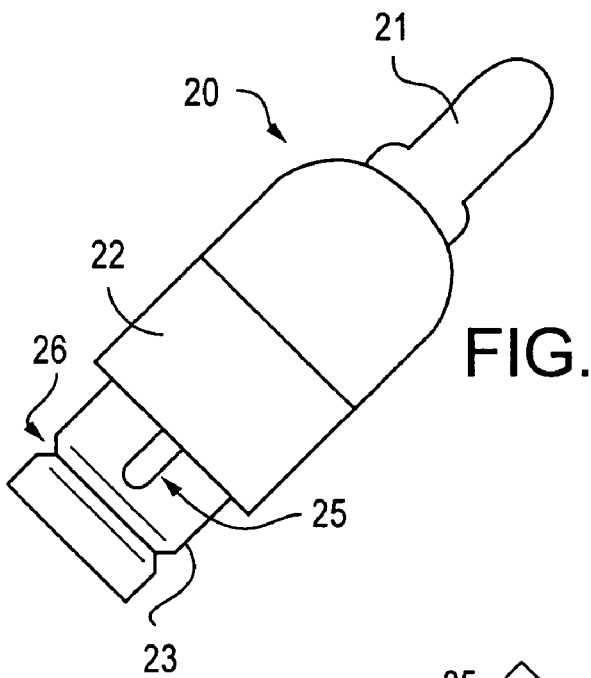
FIG. 2A is a perspective view illustrating a tip of the medical device shown in FIG. 1.
Figure 2B:
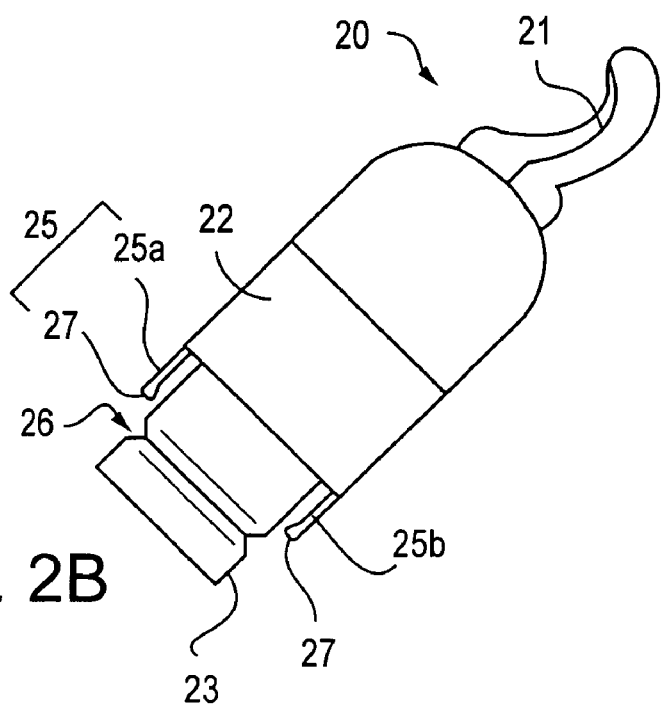
FIG. 2B is a side view of the tip shown in FIG. 2A.

In a first embodiment of the present invention, a tip 20 (as shown in FIGS. 2A and 2B, for example) may include a tip housing 22 to which the tool 21 is attached, as well as a yoke 23 for engaging with an inner shaft 30 of a tube end 40. The tip housing 22 may include a lock tab 25 for interfacing with a recess 45 of a tube end 40, and the yoke 23 may include a locking cavity (in the form of a ring groove, for example, or other suitable concavity) for removably attaching to the inner shaft 30. The lock tab may be integrally formed as a one-piece unit with the tip housing 22, and/or of a uniform material therewith, or alternatively may be heterogeneously formed separately from the tip housing 22, for example.

Further, as illustrated in FIG. 2B, for example, the tip 20 may include two or more lock tabs 25a and 25b, each of which in turn include a rounded detent 27 at the extreme end thereof. Alternatively, for example, the tip 20 may otherwise include only one lock tab 25, or several. The locking concavity or locking ring 26 may be in the form of a ring groove, for example, which is either continuous or discontinuous, and having a generally U- or V-shaped cross-section, with an angle sufficient to firmly secure the yoke 23 to the inner shaft 30 when an appropriate convexity protrudes into the locking ring 26. Preferably, the angle of the ring groove or locking ring 26 is sufficient to secure the yoke 23 to the inner shaft 30, but not to the extent that disengagement is prevented.

Alternatively, the lock tab 25 or lock tabs 25a and 25b may be attached to the outer tube 41 (see FIG. 6B, for example), and the recess may accordingly be included on the tip 20 (see the tip-based recess 451 shown in FIG. 6A), for example.

As shown in FIGS. 3A and 3B, the tube end 40 may include an outer tube 41 which includes the recess 45 formed in the outer tube 41. The recess 45 may have a generally linear shape, preferably with a generally bell-shaped mouth at the extreme edge of the outer tube 41 to guide the lock tab 25, and may include a divot 47 at the extreme end of the recess 45, into which the rounded detent 27 may protrude when the tip 20 is engaged with the tube end 40. The divot 47 may also provide tactile feedback to the user, indicating whether the tip is appropriately and fully engaged with the tube end 40 when the user is attaching the tip 20 to the tube end 40 or detaching it therefrom.

Because the recess 45 has a generally linear shape, when the lock tab 25 is inserted in the recess 45, the tabs 25 are restricted from moving in a direction perpendicular to the recess 45 (i.e., in a circumferential direction). Therefore, twisting of the tip 20 relative to the tube end 40 may be inhibited.

Further, as shown in FIG. 3B, the outer tube 41 may include two or more recesses 45 (or, alternatively, only one, for example) for respectively engaging with each of the lock tabs 25 of the tip 20. The phantom line in FIG. 3B illustrates the profile of the recess 40 and divot 47 in relation to the general outline of the outer tube 41.

In addition to the outer tube 41, the tube end 40 includes the inner shaft 30 for interfacing with the yoke 23 of the tip 20. As shown in FIGS. 4A and 4B, the inner shaft 30 may include a cuff 31 which envelopes the yoke 23 when the yoke 23 is inserted into the cuff 31, as well as an inner tube 32 that leads from the distal end of the tube 12 to the proximal end. Within the cuff 31 is a convex spring 34 or several convex springs 34a and 34b, for example, which elastically engage the locking ring 26 on the yoke 23 of the tip 20. (Although the term "locking ring" is used hereinafter for purposes of illustrating examples of medical devices according to the present invention, it is understood that according to various aspects or embodiments of the present invention the locking ring may be substituted with any appropriate locking ring such as, for example, a hemispherical hole, or a square hole, or any number thereof, in any appropriate and/or suitable formation and/or combination.)

Alternatively, for example, the spring 34 or springs 34a and 34b may be disposed on the tube end 40 or the inner shaft 30, in which case the locking ring 26 may correspondingly be disposed on the tip 20 or yoke 23, in any appropriate position or configuration to effect proper engagement of the tip 20 with the tube end 40.

As seen in FIG. 4B, in which the two phantom lines represent the outermost edge of the yoke 23 when it is inserted into the cuff 31, the protruding tips of the convex springs 34a and 34b extend inward and come in contact with the external edge of the yoke 23 when the yoke 23 is inserted into the cuff 31. As the yoke 23 slides into the cuff 31, the convex spring 34 is compressed, while in contact with the external edge of the yoke, until the locking ring 26 is brought into contact with the protruding part of the convex springs 34a and 34b. At that point, the convex springs 34a and 34b at least partially (or fully) decompress as the outer protrusions thereof enter the locking ring 26.

The convex spring 34 may have a shape or form suited for firmly holding the yoke 23 in place while the spring 34 protrudes into the locking ring 26, but not so firmly as to prevent disengagement thereof. Further, according to one aspect of the present embodiment, each of the convex springs 34a and 34b may be welded or otherwise secured (by adhesive or mechanical structure, for example) to the inner edge of the cuff 31 at two ends of the convex springs 34a and 34b, respectively, such that compression of the outer protrusion deforms the convex springs 34a and 34b at a round (or other deformably shaped) portion thereof.

FIGS. 5A and 5B illustrate a tip 20 and tube end 40 according to a second embodiment of the present invention. In the second embodiment, the tip housing 22 includes a hook-shaped lock tab 250 or hook-shaped lock tabs 250a and 250b which are analogous to the lock tab 25 of the first embodiment. However, the hook-shaped lock tab 250 of the second embodiment may include a hook-shaped end portion for firmly engaging the recess of the tube end 40, rather then the rounded detent 27 of the first embodiment.

Further, the yoke 23 according to the second embodiment may include a protruding locking ring 260 rather then the concave locking ring 26 of the first embodiment. As shown in FIG. 5B, the outer tube 41 of the tube end 40 also includes a hook-accommodating recess 450 which includes a hook-end engagement hole 470, for slidably accepting the hook-shaped lock tab 250. Unlike the first embodiment, once engaged with the tube end 40, the tip 20 of the second embodiment cannot be disengaged simply by pulling the tip 20 forward away from the tube end 40; rather, once the hook-shaped lock tab 250 is fully engaged with the hook-accommodating recess 450, disengagement of the tip 20 from the tube end 40 requires that the tip 20 first be pushed inward toward the tube end 40 until the tip of the hook-shaped lock tab 250 clears the hook-end engagement hole 470 and is then twisted (or otherwise distanced therefrom) to disengage the hook-shaped lock tab 250 out of the hook-accommodating recess 450. Accordingly, the tip 20 may be securely attached to the tube end 40 without fear of disengagement by pulling.

In the second embodiment, the locking protrusion 260 may engaged with a recess (as exemplified by spring concavities 36 in FIG. 7A, although not necessarily limited to the features illustrated therein) within the cuff 31 of the tube end 40, in a manner substantially inverse of the locking ring 26 according to the first embodiment. Elasticity for attachment and/or detachment may be provided either in the locking protrusion 260 or the recess in the tube end 40, or both, for example.

FIGS. 6A and 6B illustrate a tip 20 and tube end 40 according to a third embodiment of the present invention, respectively, in which the tip housing 22 of the tip 20 includes a tip-based recess 451 and tip-based divot 471 (analogous to the recess 45 and divot 47 according to the first embodiment), and the yoke 23 includes a hemispherical locking ring 261 or several hemispherical locking concavities 261 which do not fully extend circumferentially around the yoke 23. (It is noted that although the hemispherical locking concavities 261 are exemplified here with regards to the third embodiment, such features may be included in any appropriate embodiment of the present invention.)

Further, as shown in FIG. 6B, the outer tube 41 of the tube end 40 may include a tube end-based lock tab 251 or tube end-based lock tabs 251a and 251b, which are analogous to the lock tab 25 of the first embodiment, and which engage the tip-based recess 451 of the tip 20 according to the third embodiment. Such a configuration may be preferable where stronger materials or a more complex manufacturer are expedient on the outer tube 41 of the tube end 40, rather than on the inner tube 30, for example.

Also, because the hemispherical locking ring 261 does not extend around the entire circumference of the yoke 23, the yoke 23 is further prevented from twisting when a protrusion within the cuff 31 is extended into the hemispherical locking ring 261.

Figure 7A:
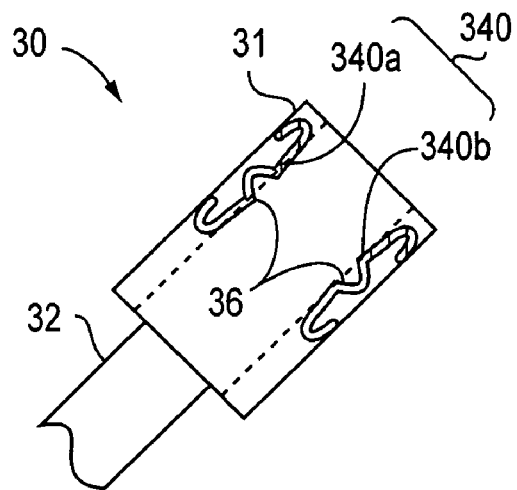
FIG. 7A is a cutaway view of the tip according to the second embodiment, illustrating an interior of the tip.
Figure 7B:
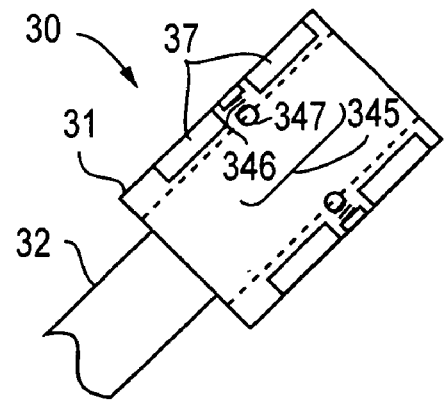
FIG. 7B is a cutaway view illustrating the interior of the tip according to the third embodiment.

FIG. 7A illustrates an inner shaft 30 according to the second embodiment, in which the concave spring 340 (or concave springs 340a and 340b, for example) is analogous to the convex spring 34 of the first embodiment, but includes a spring concavity 36 forward to accept the locking protrusion 260 (as shown in FIG. 5A) rather then extend into a locking ring 26 as in the first embodiment. Also, FIG. 7B illustrates an inner shaft 30 according to the third embodiment, which includes a coil spring 345 having a coil spring 346 with a ball protrusion 347 attached to the end of the coil spring 346. Similarly to the convex spring 34 of the first embodiment (see FIG. 4B, for example), the coil spring 345 may be elastically biased to protrude into the locking ring 26 on the yoke 23 of the tip 20 when the tip 20 is fully engaged with the tube end 40. The inner shaft 30 may further include contact pads 37 to guide and/or support the yoke 23 as it is inserted into the cuff 31, and the coil spring 345 may be a barrel pin, for example.

Figure 8A:
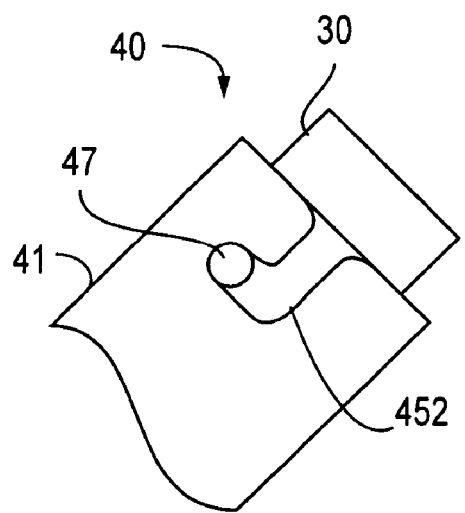
FIG. 8A is a perspective view illustrating a tube end according to a fourth embodiment of the present invention.

FIG. 8A illustrates a tube end 40 according to a fourth embodiment of the present invention, in which an L-shaped recess 452 (which is analogous to the recess 45 of the first embodiment) accepts a lock tab 25. Unlike the first embodiment, however, once the lock tab 25 of the tip 20 is inserted into the L-shaped recess 452, either the tube 12 or the tip 20 must be twisted to complete the engagement and cause, for example, the rounded detent 27 to engage the divot 47 of the fourth embodiment.

Figure 8B:
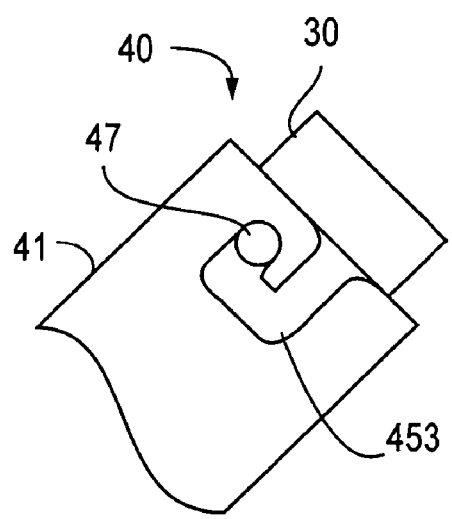
FIG. 8B is a perspective view illustrating a tube end according to a fifth embodiment of the present invention.

Similarly, a tube end 40 according to a fifth embodiment of the present invention is illustrated in FIG. 8B. A J-shaped recess 453 may be similar to the L-shaped recess 452 of the fourth embodiment, but has a substantially J-shaped outline.

As the lock tab 25 is guided along the J-shaped recess 453, once the rounded detent 27 enters the divot 47 the disengagement of the tip 20 from the tube end 40 is inhibited (as well as torsion thereof until the tip 20 is pushed inward toward the tube end 40 such that the rounded detent 27 disengages from the divot 47 and the tip 20 is appropriately slid along the J-shaped recess 453 and pulled outward therefrom. As an advantage, inadvertant or unwanted twisting, as well as unintentional disengagement of the tip 20 from the tube end 40, may be prevented.

Figure 9A:
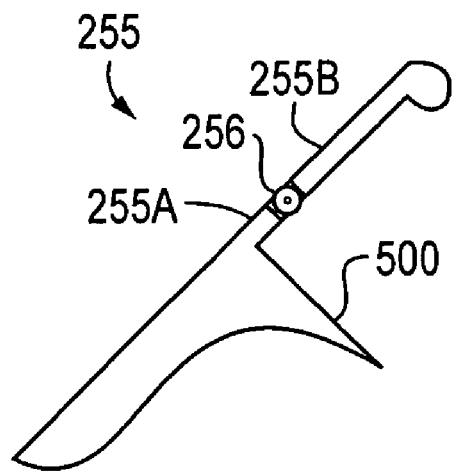
FIG. 9A is an enlarged view of a lock tab according to a sixth embodiment of the present invention.
Figure 9B:
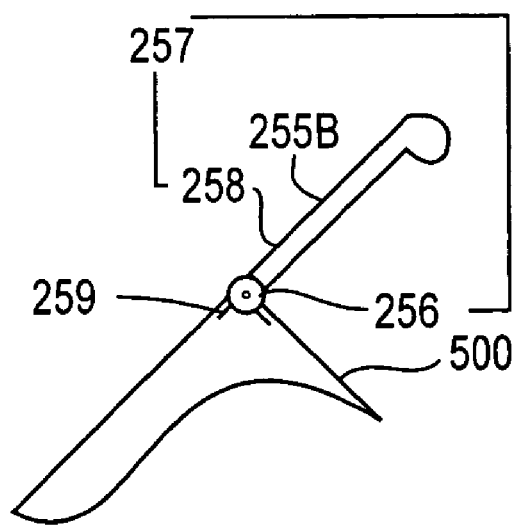
FIG. 9B is an enlarged view of the lock tab according to a seventh embodiment of the present invention.

FIGS. 9A and 9B respectively illustrate sixth and seventh embodiments of the present invention, in which a mid-hinged lock tab 255 or base-hinged lock tab 257 (both of which are analogous to the lock tab 25 of the first embodiment and/or the tube end-based lock tab 251 of the third embodiment), respectively, includes a hinge 256 either at the mid-portion or base thereof. Unlike the above-discussed embodiments, in which the lock tabs 25 are urged inward toward the center of the tube 12 by elasticity inherent to the material forming the lock tab 25 and/or outer tube 41 or tip housing 22 when the lock tabs 25 are elastically deformed outward, the sixth and seventh embodiments may utilize a torque spring 259 to bias the lock tab inward.

As shown in FIG. 9A, in which the base 500 represents any appropriate body from which the lock tab 25 protrudes, a mid-hinged lock tab 255 includes a hinge 256 connecting a first member 255a to a second member 255b. In the seventh embodiment, as shown in FIG. 9B, for example, the base-hinged lock tab 257 includes a single tab 258 connected to the base 500 by the hinge 256. The torque spring 259 exerts an inward-biased force on the tab 258.

An advantage of the seventh and eight embodiments is that the torque spring 259 may selected to have a particular strength, and material fatigue of the material (which may be plastic or metal, for example) of the lock tab 255 or 257 cause by repeated flexing as the tip 20 is repeatedly attached as detached from the tube end 40, or by flexing beyond the elastic limit of the material, may be prevented. Further, a user may disengage the lock tab 257 or 255 by using a spring-release mechanism (not shown), whereas the tip 20 of the first embodiment must be disengaged by pulling the tip 20 from the tube end 40 with moderate force.

It is noted that the foregoing examples have been provided merely for the purpose of explanation and are in no way to be construed as limiting of the present invention. While the present invention has been described with reference to certain embodiments, it is understood that the words which have been used herein are words of description and illustration, rather then words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A medical device, comprising:
a tube end including an outer tube and an inner shaft slidable along an axial length of and in relation to the outer tube;
a recess disposed in the outer tube of the tube end;
an instrument removably connectable to the tube end and comprising:
a lock tab removably connectable with the recess of the tube end, and
a yoke removably connectable with the inner shaft of the tube end;
a locking ring located on one of the yoke and the inner shaft; and
a spring located on the other of the yoke and the inner shaft and configured to lockably attach to the locking ring such that the spring and the locking ring removably attach the inner shaft to the yoke.

2. The medical device according to claim 1, further comprising:
another recess disposed in the outer tube of the tube end; and
another lock tab disposed on the tip and configured to engage with the another recess of the outer tube of the tube end.

3. The medical device according to claim 1, further comprising:
a cuff attached to the inner shaft and including the spring fixedly attached to an interior of the cuff, the cuff configured to receive the yoke,
wherein the spring engages the locking ring when the tip is engaged with the tube end.

4. The medical device according to claim 1, further comprising another spring configured to engage with the locking ring.

5. The medical device according to claim 1, further comprising a generally rounded detent portion disposed at an extremity of the lock tab of the tip and configured to engage with a divot disposed at an extremity of the recess of the outer tube of the tube end.

6. The medical device according to claim 1, wherein the locking ring has a notched profile and generally extends around a circumference of the yoke.

7. The medical device according to claim 1, wherein the recess of the outer tube of the tube end has a shape generally similar to a letter 'L'.

8. The medical device according to claim 1, wherein the recess of the outer tube of the tube end has a generally linear outline leading from an edge of the outer tube and configured to resist twisting of the tip relative to the tube end.

9. The medical device according to claim 1, wherein the lock tab is radially biased toward a longitudinal center of the tip.

10. A medical device, comprising:
a tube end including an outer tube end and an inner shaft slidable along an axial length of and in relation to the outer tube;
an instrument tip removably connectable to the tube end and including a yoke configured to removably connect to the inner shaft of the tube end;
a recess located on one of the tip and the outer tube end;
a lock tab located on the other of the tip and the outer tube end and configured to removably connect with the recess; and
a lock comprising:
a protrusion located on one of the tube end and the yoke; and
a concavity located on the other of the tube end and the yoke,
wherein the protrusion and the concavity are configured to lockably engage each other to removably secure the tip to the tube end.

11. The medical device according to claim 10, wherein the protrusion is disposed on the yoke and includes a spring configured to elastically extend toward the outer tube of the tube end.

12. The medical device according to claim 10, wherein the concavity is located in the tube end and includes a spring configured to receive the protrusion, and the protrusion is disposed on the yoke.

13. The medical device according to claim 12, further comprising:
a cuff attached to the inner shaft of the tube end and including the concavity located in an interior of the cuff, the cuff configured to receive the yoke,
wherein the protrusion extends into the concavity when the tip is engaged with the tube end.

14. The medical device according to claim 10, further comprising:
another recess located on one of the tip and the outer tube end; and
another lock tab located on the other of the tip and the outer tube end and configured to engage with the another recess.

15. The medical device according to claim 10, further comprising another protrusion located on one of the tube end and the yoke and configured to engage the concavity.

16. The medical device according to claim 10, further comprising:
a divot disposed at an extremity of the recess; and
a generally rounded detent portion disposed at an extremity of the lock tab and configured to engage the divot.

17. The medical device according to claim 10, wherein the recess has a shape generally similar to a letter 'L'.

18. The medical device according to claim 10, wherein the recess has a generally linear outline and is configured to resist twisting of the tip relative to the tube end.

19. The medical device according to claim 10, wherein the lock tab is radially biased toward a radial center of the other of the tip or the tube end.

20. The medical device according to claim 10, wherein the lock tab is connected to the outer tube of the tube end, and the recess is disposed in the tip.

21. A medical device, comprising:
an outer tube having an open proximalmost end and an open distalmost end, the open proximalmost and open distalmost ends in communication with each other via a lumen;
an inner shaft positioned within the outer tube and extending generally parallel with the outer tube, wherein the outer tube and inner shaft collectively define a tube end positioned at a distal end thereof;
a recess in the outer tube at the tube end;
an instrument removably connectable to the tube end and comprising:
a lock tab removably connectable with the recess, and
a yoke removably connectable with the inner shaft at the tube end;
a locking ring located on one of the yoke and the inner shaft; and
a spring located on the other of the yoke and the inner shaft and configured to lockably connect to the locking ring such that the spring and the locking ring removably attach the inner shaft to the yoke.

22. The medical device according to claim 21, further comprising:
another recess disposed in the outer tube at the tube end; and
another lock tab disposed on the tip and configured to removably connect to the another recess of the outer tube at the tube end.

23. The medical device according to claim 21, further comprising:
a cuff attached to the inner shaft and including the spring attached to an interior of the cuff, the cuff configured to receive the yoke,
wherein the spring removably connects to the locking ring when the tip is connected to the tube end.

24. The medical device according to claim 21, further comprising another spring configured to removably connect the locking ring.

25. The medical device according to claim 21, further comprising a generally rounded detent disposed at an extremity of the lock tab of the tip and configured to removably connect with a divot disposed at an extremity of the recess.

26. The medical device according to claim 21, wherein the locking ring has a notched profile and generally extends about a circumference of the yoke.

27. The medical device according to claim 21, wherein the recess of the outer tube is generally 'L' shaped.

28. The medical device according to claim 21, wherein the recess of the outer tube has a generally linear outline leading from an edge of the outer tube and configured to resist twisting of the tip relative to the tube end.

29. The medical device according to claim 21, wherein the lock tab is radially biased toward a longitudinal center of the tip.

30. A medical device, comprising:
an outer tube having an open proximalmost end and an open distalmost end, the open proximalmost and open distalmost ends in communication with each other via a lumen;
an inner shaft positioned within the lumen and extending generally parallel with the outer tube, wherein the outer tube and inner shaft collectively define a tube end positioned at a distal end thereof;
an instrument tip removably connectable to the tube end and including a yoke configured to removably connect to the inner shaft;
a recess located on one of the tip and the outer tube at the tube end;
a lock tab located on the other of the tip and the outer tube and configured to removably connect with the recess; and
a lock comprising:
a protrusion located on one of the tube end and the yoke; and
a concavity located on the other of the tube end and the yoke, wherein the protrusion and the concavity are configured to removably lockably engage each other to removably secure the tip to the tube end.

31. The medical device according to claim 30, wherein the protrusion is disposed on the yoke and includes a spring configured to elastically extend toward the outer tube of the tube end.

32. The medical device according to claim 30, wherein the concavity is located in the tube end and includes a spring configured to receive the protrusion, and the protrusion is disposed on the yoke.

33. The medical device according to claim 30, further comprising:
another recess located on one of the tip and the outer tube at the tube end; and another lock tab located on the other of the tip and the outer tube and configured to removably connect to the another recess.

34. The medical device according to claim 32, further comprising:
a cuff attached to the inner shaft and including the concavity located in an interior of the cuff, the cuff configured to receive the yoke,
wherein the protrusion extends into the concavity when the tip is connected with the tube end.

35. The medical device according to claim 30, further comprising another protrusion located on one of the tube end and the yoke and configured to removably connect with the concavity.

36. The medical device according to claim 30, further comprising:
a divot disposed at an extremity of the recess; and
a generally rounded detent disposed at an extremity of the lock tab and configured to connect with the divot.

37. The medical device according to claim 30, wherein the recess is generally 'L' shaped.

38. The medical device according to claim 30, wherein the recess has a generally linear outline and is configured to resist twisting of the tip relative to the tube end.

39. The medical device according to claim 30, wherein the lock tab is radially biased toward a radial center of the other of the tip or the tube end.

40. The medical device according to claim 30, wherein the lock tab is connected to the outer tube, and the recess is disposed in the tip.

* * * * *